US 7,189,206 B2

(12) United States Patent
Quick et al.

(10) Patent No.: US 7,189,206 B2
(45) Date of Patent: Mar. 13, 2007

(54) BIOPSY DEVICE WITH INNER CUTTER

(75) Inventors: Richard L. Quick, Mission Viejo, CA (US); Frank Louw, Carlsbad, CA (US); Paul Lubock, Laguna Niguel, CA (US); Martin V. Shabaz, Lake Forest, CA (US)

(73) Assignee: SenoRx, Inc., Aliso Viejo, CA (US)

( * ) Notice: Subject to any disclaimer, the term of this patent is extended or adjusted under 35 U.S.C. 154(b) by 365 days.

(21) Appl. No.: 10/374,915

(22) Filed: Feb. 24, 2003

(65) Prior Publication Data

US 2004/0167427 A1     Aug. 26, 2004

(51) Int. Cl.
*A61B 10/00* (2006.01)
(52) U.S. Cl. ..................................... 600/564
(58) Field of Classification Search ........ 600/564–568; 606/167, 170
See application file for complete search history.

(56) References Cited

U.S. PATENT DOCUMENTS

| | | |
|---|---|---|
| 3,326,785 A | 6/1967 | Williams |
| 3,805,791 A | 4/1974 | Seuberth et al. |
| 3,844,272 A | 10/1974 | Banko |
| 3,910,279 A | 10/1975 | Okada et al. |
| 3,945,375 A | 3/1976 | Banko et al. |
| 4,007,732 A | 2/1977 | Kvavle et al. |
| 4,243,048 A | 1/1981 | Griffin |
| 4,294,254 A | 10/1981 | Chamness |
| 4,311,143 A | 1/1982 | Komiya |
| 4,362,160 A | 12/1982 | Hiltebrandt |
| 4,503,855 A | 3/1985 | Maslanka |

(Continued)

FOREIGN PATENT DOCUMENTS

EP      0 255 123      2/1988

(Continued)

OTHER PUBLICATIONS

Timothy L. Micklos, Purcutaneous Biopsy Techniques, *Manual of Oncologic* Therapeutics (1989/1990), pp. 39-42.

(Continued)

*Primary Examiner*—Max F. Hindenburg
*Assistant Examiner*—Brian Szmal
(74) *Attorney, Agent, or Firm*—Edward J. Lynch; Duane Morris LLP

(57) ABSTRACT

The invention is directed to devices and methods for accessing a desired target site within a patient's body and for separating and collecting a tissue specimen from the target site. The device includes a probe member or cannula with a penetrating distal tip, and a tissue cutting member which is disposed within the probe member to cut a tissue specimen from supporting tissue at the biopsy site. This probe is releasably secured to a housing to provide a plurality of discrete orientations of the probe about its longitudinal axis. Vacuum may be provided to the inner lumen of the cutting member to transport tissue through the inner lumen thereof. Rotation (and optionally longitudinal reciprocation) of the tissue cutter is effective to separate a tissue specimen from surrounding tissue at the target site. Vacuum or fluid pressure may be used to move the specimen cut from the target site proximally within the inner lumen defined at least in part by the culling member for collection.

39 Claims, 10 Drawing Sheets

U.S. PATENT DOCUMENTS

| | | |
|---|---|---|
| 4,576,162 A | 3/1986 | McCorkle |
| 4,682,606 A | 7/1987 | DeCaprio |
| 4,926,858 A | 5/1990 | Gifford, III et al. |
| 5,047,027 A | 9/1991 | Rydell |
| 5,059,204 A | 10/1991 | Lawson et al. |
| 5,064,424 A | 11/1991 | Bitrolf |
| 5,080,660 A | 1/1992 | Buelna |
| 5,085,659 A | 2/1992 | Rydell |
| 5,133,359 A | 7/1992 | Kedem |
| 5,133,360 A | 7/1992 | Spears |
| RE34,056 E | 9/1992 | Lindgren et al. |
| 5,158,561 A | 10/1992 | Rydell et al. |
| 5,217,458 A | 6/1993 | Parins |
| 5,320,613 A | 6/1994 | Houge et al. |
| 5,335,671 A | 8/1994 | Clement |
| 5,441,503 A | 8/1995 | Considine et al. |
| 5,470,308 A | 11/1995 | Edwards et al. |
| 5,477,862 A | 12/1995 | Haga |
| 5,488,958 A | 2/1996 | Topel et al. |
| 5,507,743 A | 4/1996 | Edwards et al. |
| 5,526,822 A | 6/1996 | Burbank et al. |
| 5,527,331 A | 6/1996 | Kresch et al. |
| 5,538,010 A | 7/1996 | Darr et al. |
| 5,595,185 A | 1/1997 | Erlich et al. |
| 5,607,389 A | 3/1997 | Edwards et al. |
| 5,649,547 A | 7/1997 | Ritchart et al. |
| 5,687,739 A | 11/1997 | McPherson et al. |
| 5,769,086 A | 6/1998 | Richart et al. |
| 5,775,333 A | 7/1998 | Burbank et al. |
| 5,782,775 A | 7/1998 | Milliman et al. |
| 5,797,907 A | 8/1998 | Clement |
| 5,810,806 A | 9/1998 | Ritchart et al. |
| 5,814,044 A | 9/1998 | Hooven |
| 5,846,513 A | 12/1998 | Carrol et al. |
| 5,848,978 A | 12/1998 | Cecchi |
| 5,857,981 A | 1/1999 | Bucalo et al. |
| 5,857,982 A | 1/1999 | Milliman et al. |
| 5,876,340 A | 3/1999 | Tu et al. |
| 5,882,316 A | 3/1999 | Chu et al. |
| 5,902,272 A | 5/1999 | Eggers et al. |
| 5,913,857 A | 6/1999 | Ritchart et al. |
| 5,925,044 A | 7/1999 | Hofmann et al. |
| 5,928,164 A | 7/1999 | Burbank et al. |
| 5,947,964 A | 9/1999 | Eggers et al. |
| 5,954,670 A | 9/1999 | Baker |
| 5,964,716 A | 10/1999 | Gregoire et al. |
| 5,980,469 A | 11/1999 | Burbank et al. |
| 5,984,919 A | 11/1999 | Hilal et al. |
| 5,997,560 A | 12/1999 | Miller |
| 6,036,681 A | 3/2000 | Hooven |
| 6,050,955 A | 4/2000 | Bryan et al. |
| 6,056,700 A | 5/2000 | Burney et al. |
| 6,120,462 A | 9/2000 | Hibner et al. |
| 6,142,955 A | 11/2000 | Farascioni et al. |
| 6,258,000 B1 | 7/2001 | Liechty, II |
| 6,261,241 B1 | 7/2001 | Burbank et al. |
| 6,277,083 B1 | 8/2001 | Eggers et al. |
| 6,312,429 B1 | 11/2001 | Lubock et al. |
| 6,514,215 B1 | 2/2003 | Ouchi |
| 6,514,248 B1 | 2/2003 | Eggers et al. |
| 6,540,695 B1 | 4/2003 | Burbank et al. |
| 6,689,145 B2 | 2/2004 | Lee et al. |
| 6,758,824 B1 * | 7/2004 | Miller et al. ................. 600/568 |
| 2003/0004407 A1 | 1/2003 | Carroll et al. |
| 2003/0125639 A1 * | 7/2003 | Fisher et al. ................. 600/564 |

FOREIGN PATENT DOCUMENTS

| | | |
|---|---|---|
| EP | 0 601 709 | 6/1994 |
| EP | 0 769 281 | 4/1997 |
| EP | 0 919 190 | 6/1999 |
| EP | 0 966 925 | 12/1999 |
| EP | 0 970 658 | 1/2000 |
| WO | 98/08441 | 3/1998 |
| WO | WO 0 858 774 A2 | 8/1998 |
| WO | WO 99 44506 A | 9/1999 |
| WO | WO 00/12009 | 3/2000 |
| WO | WO 00 16697 | 3/2000 |
| WO | WO 02/22023 | 3/2002 |
| WO | WO 2005/063126 | 7/2005 |

OTHER PUBLICATIONS

Whitman et al., Coaxial Core Needle Biopsy Under Mammographic Guidance: Indications and Applications, AJR:171, Jul. 1998, pp. 67-70.

International Search Report for PCT/US2004/043021, mailed Jul. 26, 2005.

Written Opinion of the International Searching Authority for PCT/US2004/043021, mailed Jul. 26, 2005.

International Search Report for PCT/US2005/027071 mailed Dec. 2, 2005.

International Search Report in PCT/US04/05023 mailed Nov. 29, 2006.

Written Opinion of the International Searching Authority in PCT/US04/05023 mailed Nov. 29, 2006.

* cited by examiner

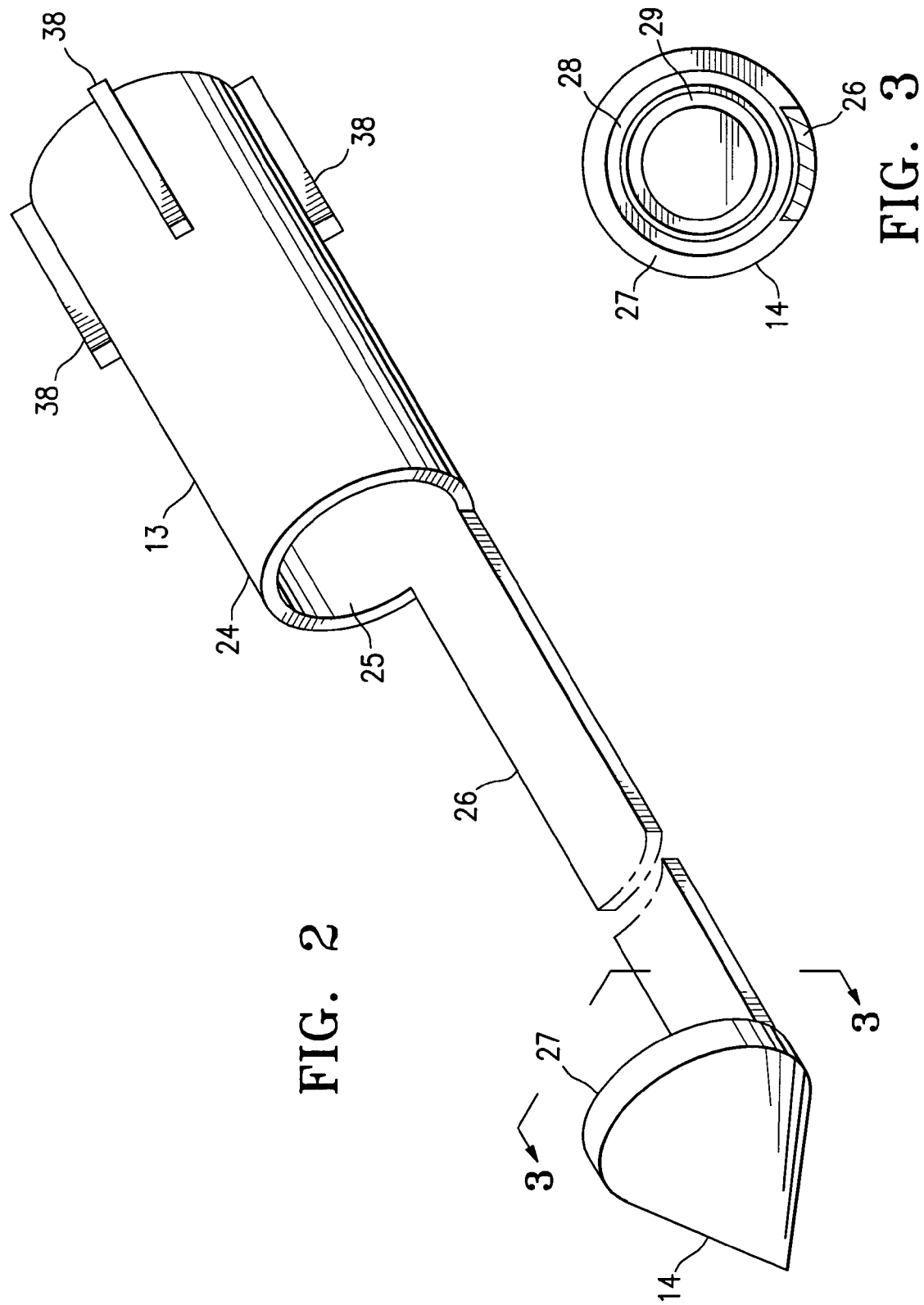

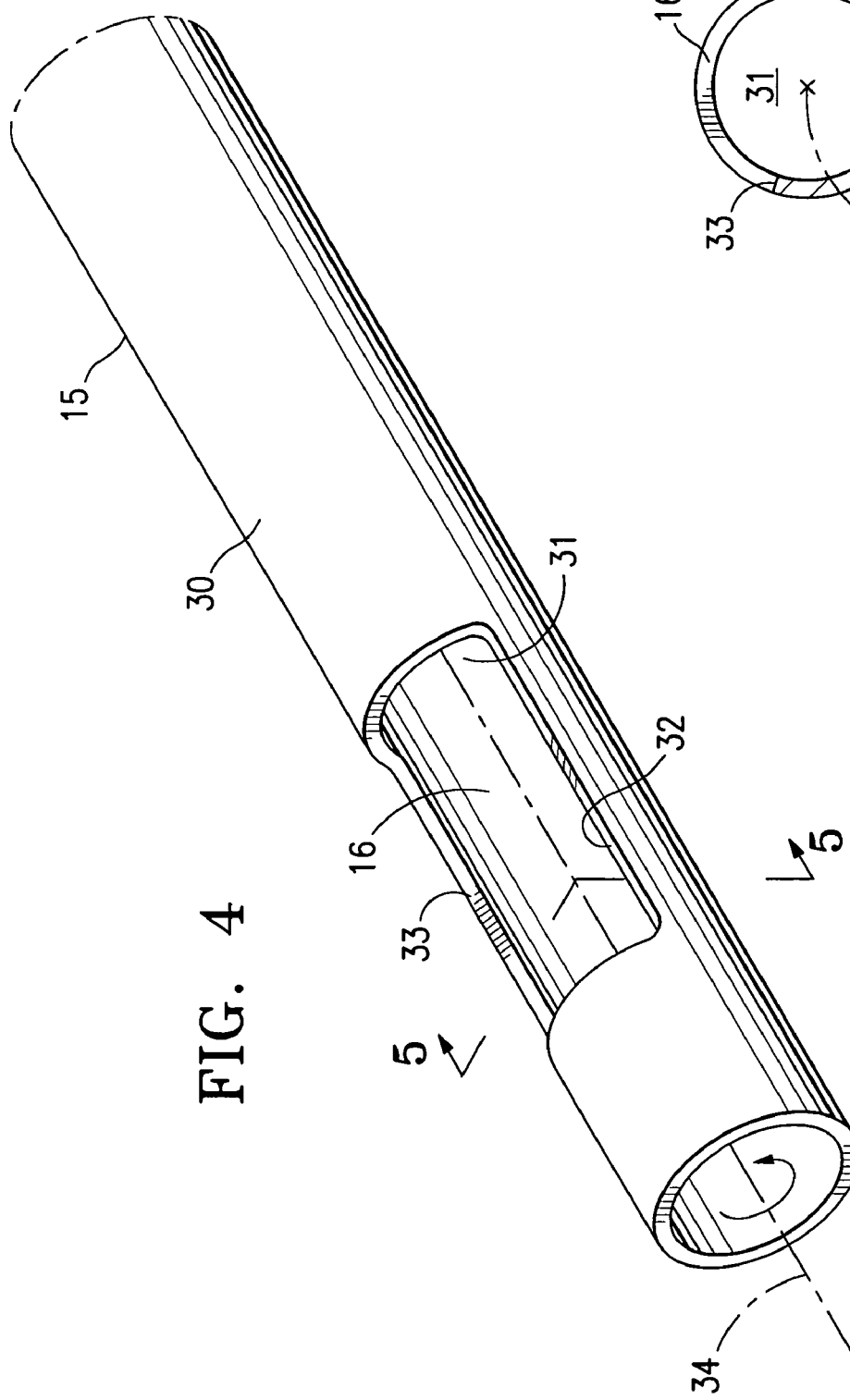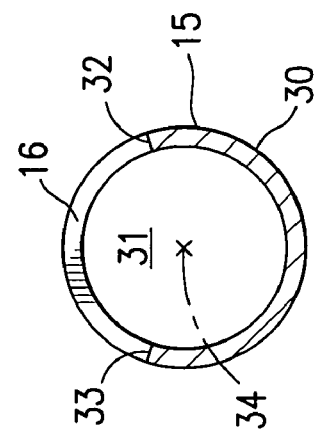
FIG. 4
FIG. 5

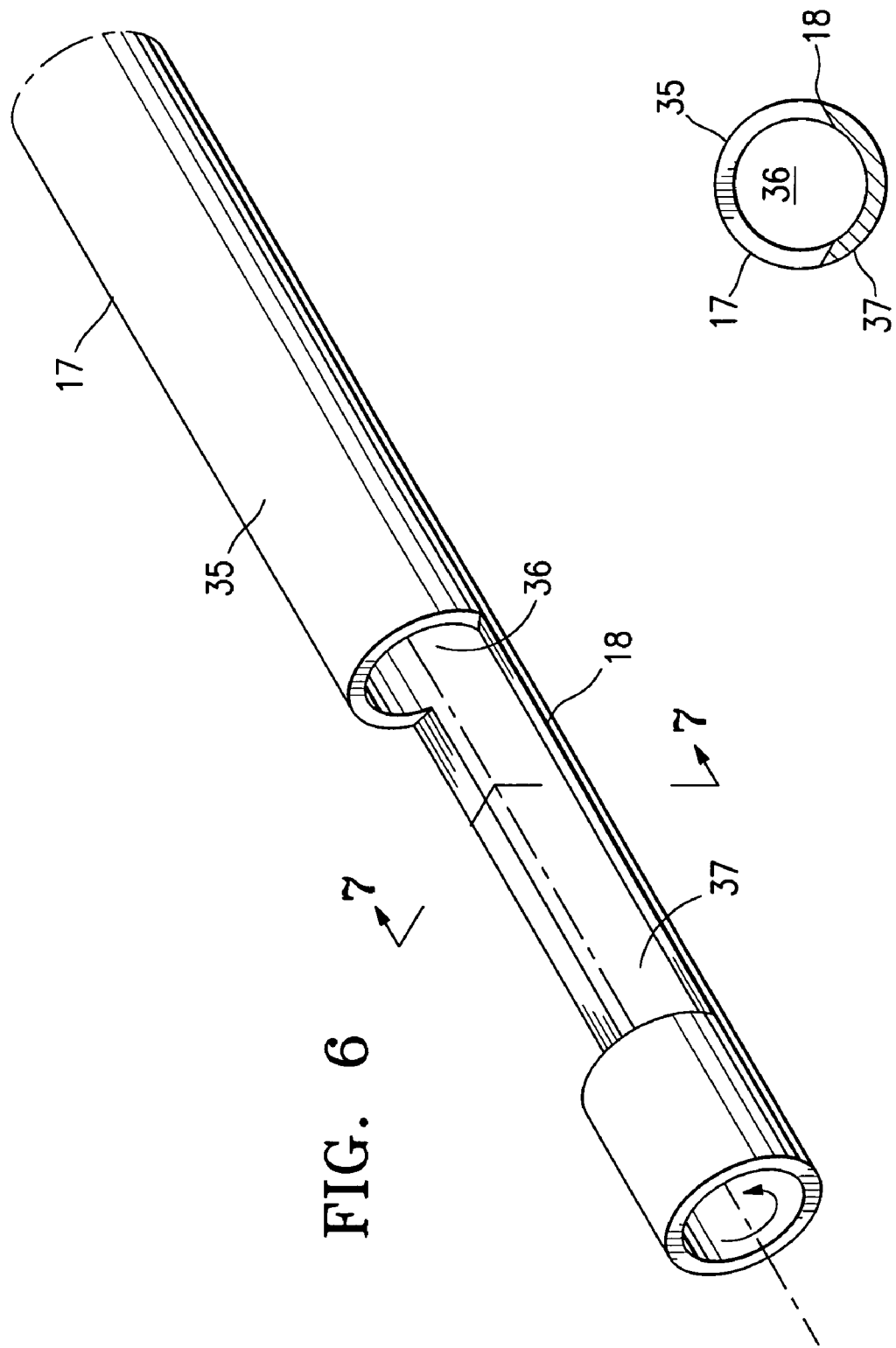

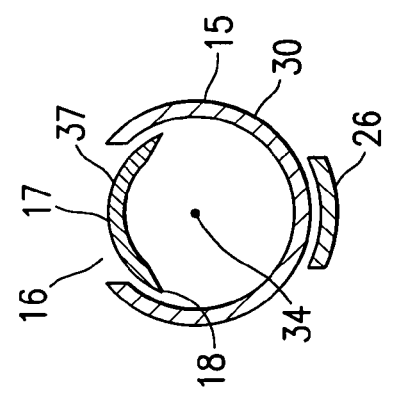
FIG. 9A
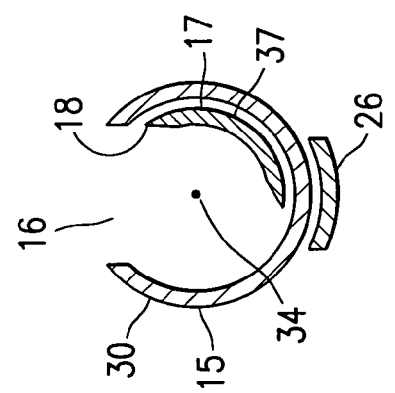
FIG. 9B
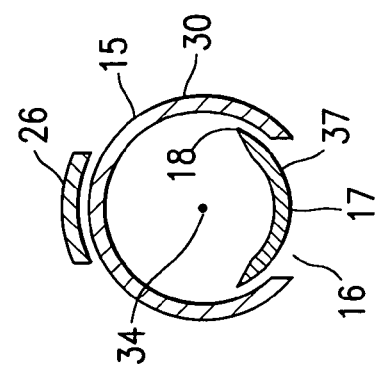
FIG. 10A
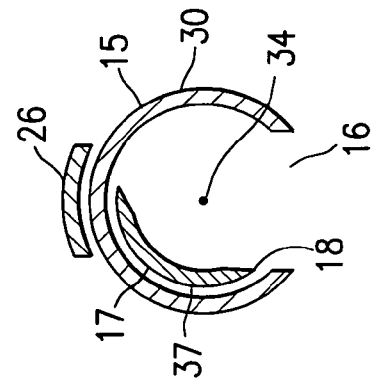
FIG. 10B
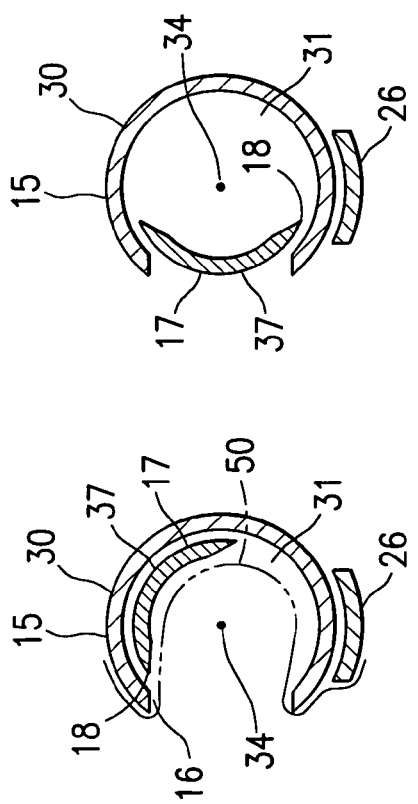
FIG. 11A
FIG. 11B
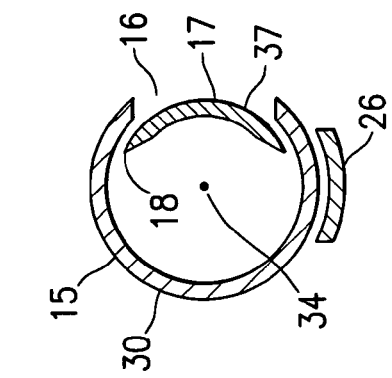
FIG. 12A
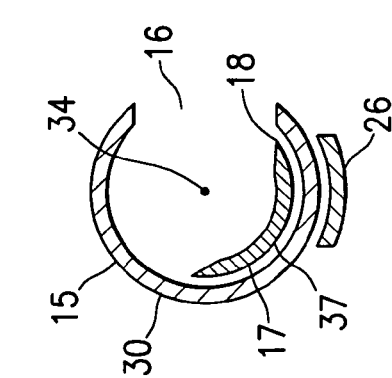
FIG. 12B

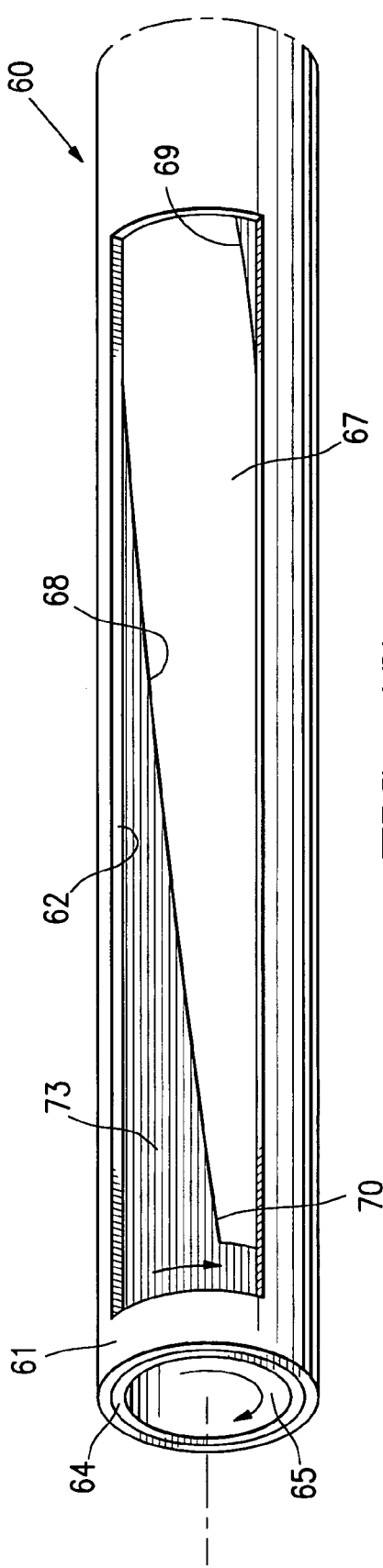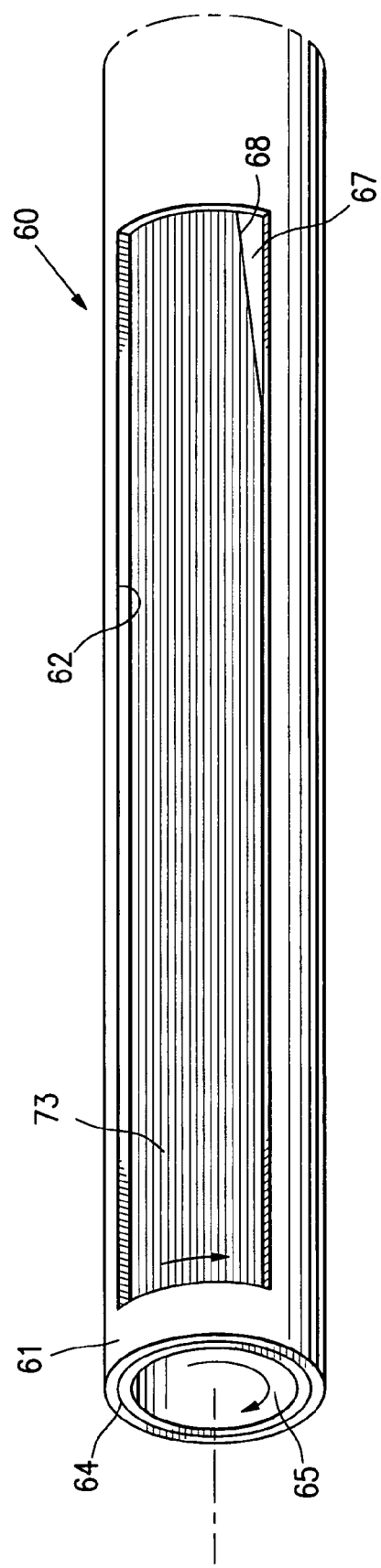
FIG. 17
FIG. 18

BIOPSY DEVICE WITH INNER CUTTER

FIELD OF THE INVENTION

The present invention relates generally to the field of biopsy devices and the methods of using such devices. More specifically, it relates to a device and method for accessing and removing pathologically suspect tissue from within a patient's body.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to extract the biopsy specimen therefrom.

Electrosurgical techniques have been used in a variety of biopsy procedures. In electrosurgery, high frequency electrical energy is typically applied to patient tissue through an active electrode, the electrical circuit being completed by a return electrode in contact with the patent's tissue. Electrical energy flowing through the tissue from the active electrode is effective to ablate tissue near the active electrode, forming an opening in the tissue and so allowing insertion of the instrument into a patient's body. A return electrode may be placed on the exterior of the patient's body or may be intracorporeally disposed. The return electrode is typically attached to the patient at a point remote from where the primary or active electrode contacts the tissue. However, in the case of a bipolar electrode for example, the return electrode may be disposed near to the active electrode. An electrosurgical biopsy instrument is disclosed and claimed in U.S. patent application Ser. No. 09/159,467 for "Electrosurgical Biopsy Device and Method," now U.S. Pat. No. 6,261,241, assigned to the assignee of the subject application, and which is hereby incorporated by reference in its entirety.

SUMMARY OF THE INVENTION

This invention is directed to biopsy devices and methods for accessing and collecting a tissue specimen that provides access to a targeted biopsy site and provides for the separation of the tissue from supporting tissue at the targeted biopsy site and the capture of the separated tissue specimen.

An elongated tissue biopsy device having features of the invention includes an elongated probe with an outer member having a tissue penetrating distal tip, a proximal tubular portion, an inner lumen extending within the tubular portion and an opened section in a distal portion which provides access to tissue at the targeted biopsy site. The probe includes an elongated tissue-cutting member which is slidably disposed within the inner lumen of the outer member and is provided with a tissue cutting surface which is configured to sever tissue extending into the probe through an aperture. The cutting surface on the tissue cutting member may be a longitudinally oriented cutting surface which is rotationally or rotationally and longitudinally moved to cut a tissue specimen or the cutting surface may be circumferentially oriented on the distal end of the cutting member which is rotationally and longitudinally moved to sever specimen tissue from supporting tissue at the targeted biopsy site. The cutting member may be configured to provide longitudinal reciprocation in addition to rotation in the case of longitudinally oriented cutting surfaces and rotational reciprocation in addition to longitudinal motion in the case of circumferentially oriented cutting surfaces.

The cutting member has an inner lumen extending to the proximal end thereof for tissue specimen removal. Mechanical withdrawal of the tissue specimen may be employed or the proximal end of the cutting member may be configured to be in fluid communication with a vacuum source to aspirate the severed tissue specimen through the inner lumen of the cutter member to a tissue collection station. A fluid directing conduit may be provided in the inner lumen of the cutting member with a discharge port that is distal to the tissue specimen to deliver pressurized fluid distal to a severed tissue specimen to aid in transporting the specimen proximally through the inner lumen of the cutting member to the tissue collection station. In this manner, the mechanical withdrawal and/or the vacuum on the proximal end of the specimen and a positive pressure on the distal end of the specimen move the specimen through the inner lumen of the cutting member to a specimen collection station.

The probe is secured, preferably releasably secured, to a drive housing provided with at least one drive unit. The tissue cutter is operatively connected to the at least one drive unit to provide the desired cutting motion. The proximal end of the outer cannula is releasably secured to the drive housing so that the orientation of the outer cannula with respect to the housing can be selected before the probe is inserted into the patient.

The probe may be provided with a tubular tissue accessing cannula which is concentrically disposed between the outer member and the tissue cutting member and a distal portion of the accessing cannula is provided with a tissue accessing aperture. The tissue accessing cannula is connected by its proximal end to a drive unit within the housing to rotate the cannula to adjust the orientation of the tissue receiving aperture about the longitudinal axis of the accessing cannula. A proximal extremity of the cutting member is connected to a second drive unit or units to effect the rotation and any longitudinal motion desired for cutting the tissue specimen A method of cutting and collecting a biopsy tissue specimen from a targeted biopsy site of a patient includes
 a) advancing an elongated tissue biopsy device having features of the invention at least partially into tissue at a desired site within the patient's body with the tissue penetrating distal tip of the outer cannula distal to the tissue to be separated from the target site;
 b) exposing the inner lumen of the accessing cannula to tissue through the accessing aperture;
 c) applying a vacuum to the inner lumen of the accessing cannula to draw tissue into the inner lumen thereof; and
 d) separating a tissue specimen from the target site by rotating (or rotating and longitudinally reciprocating) the tissue-cutting member to cut a tissue specimen from supporting tissue at the biopsy site which extends into the inner lumen. Vacuum may be applied to the inner lumen of the cutting member, to pull or aspirate the tissue sample proximally. In addition, or alternatively, fluid pressure may be applied to a distal portion of the inner lumen distal to the specimen to push the tissue specimen proximally or the specimen may be mechanically withdrawn. Fluid pressure may include pressure from a liquid delivered into the interior of the device, such as a physiological saline solution, and may include a gas, such as pressurized carbon dioxide, nitrogen or air, delivered into the interior of the device. The tissue specimen may then be withdrawn from the patient for subsequent pathological examination.

After acquisition of a tissue specimen or specimens, the biopsy device may be withdrawn from the patient and the specimen removed. However, vacuum and/or fluid pressure or mechanical devices may be sufficient to remove the tissue specimen from the patient without removal of the device from the patient's body.

The outer member of the probe provides the support for the probe to enable precise location of the accessing port to the desired location at the target site with its longitudinal orientation being preset before the device is introduced into the patient. If an accessing cannula is provided with the biopsy device, the accessing cannula is rotated to further position the tissue accessing aperture to the desired specimen tissue and also to relocate the accessing aperture for taking further specimens. The cutting member quickly and cleanly severs the tissue specimen from the supporting tissue to provide a better tissue specimen for pathological examination.

These and other advantages of the invention will become more apparent from the following detailed description of the invention and the accompanying exemplary drawings.

BRIEF DESCRIPTION OF THE DRAWINGS

FIG. 2 is a perspective view of the distal portion of the outer member or cannula of the biopsy device shown in the FIG. 1.

FIG. 3 is a transverse view, partially in section, of the proximal end of the distal tip of the outer member shown in FIG. 2 taken along the lines 3—3.

FIG. 4 is a perspective view of the distal portion of the tissue accessing cannula of a biopsy device shown in FIG. 1.

FIG. 5 is a transverse cross-sectional view of the tissue accessing cannula shown FIG. 4 taken along the lines 5—5.

FIG. 6 is a perspective view of the distal portion of the tissue cutter of the biopsy device shown in FIG. 1.

FIG. 7 is a transverse cross-sectional view of the tissue cutter shown in FIG. 6 taken along the lines 7—7.

FIGS. 9A and 9B are schematic transverse cross-sectional views of the probe shown in FIG. 1 in open and closed configurations respectively with the aperture of the tissue accessing device opening to the left.

FIGS. 10A and 10B are schematic transverse cross-sectional views of the probe shown in FIG. 1 in open and closed configurations respectively with the aperture of the tissue accessing device opening upwardly.

FIGS. 11A and 11B are schematic transverse cross-sectional views of the probe shown in FIG. 1 in open and closed configurations respectively with the aperture of the tissue accessing device opening to the right.

FIGS. 12A and 12B are schematic transverse cross-sectional views of the probe shown in FIG. 1 in open and closed configurations respectively with the aperture of the tissue accessing device opening downwardly.

FIG. 17 is a perspective view of the probe shown in FIG. 13 further rotated from that shown in FIG. 16.

FIG. 18 is a perspective view of the probe shown in FIG. 13 with the aperture of the outer member almost closed.

DETAILED DESCRIPTION OF THE INVENTION

Figure 1:
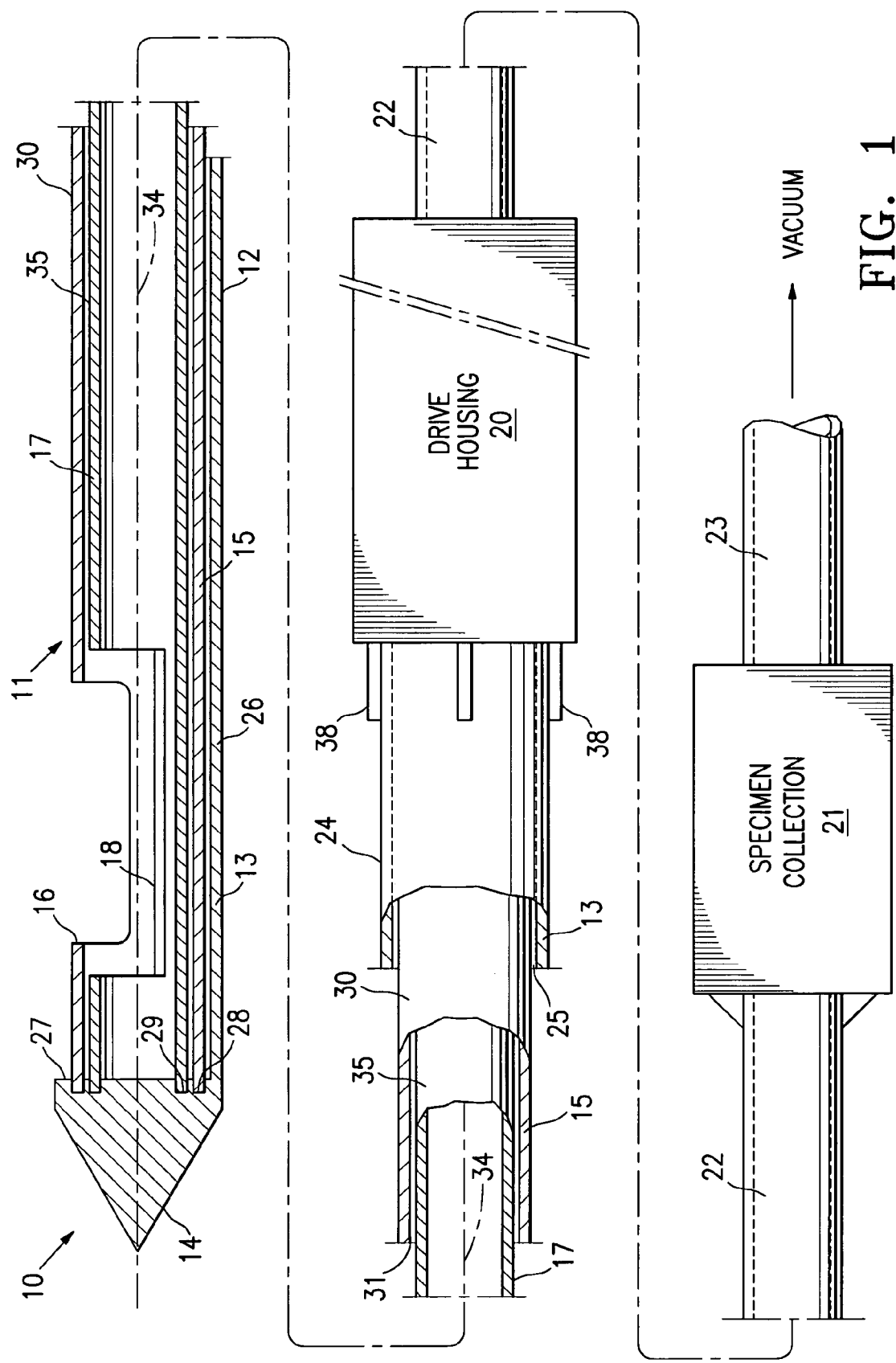
FIG. 1 is an elevational view, partially in section, of an elongated tissue biopsy device having features of the invention.

FIGS. 1–7 illustrate a system 10 which includes a biopsy device 11 embodying features of the invention. The biopsy device 11 generally includes an elongated shaft or probe 12 having an outer member or cannula 13 with a tissue penetrating tip 14 on the distal end thereof, a tissue accessing cannula 15 with a tissue receiving aperture 16 and a tissue-cutting member 17 with a tissue cutting surface 18. The proximal end of the outer member 13 is releasably secured to a drive housing 20 to provide a plurality of discrete orientations to the outer member 13. The housing 20 is provided with a drive unit (not shown) configured to provide motion to the tissue accessing cannula 15 and the tissue cutter 17. A tissue specimen collection station 21 is connected in a fluid flow relationship with the tissue cutter 17 through conduit 22 and is connected to a vacuum source (not shown) through conduit 23.

As shown in more detail in FIG. 2 the outer member 13 has an elongated tubular body 24 with an inner lumen 25 which is configured to receive and support the accessing cannula 15. The distal end of inner lumen 25 opens to the tissue accessing space between the distal end of the tubular body 24 and the proximal end of tissue penetrating tip 14. A connecting strut or wall portion 26 extends between the tissue penetrating distal tip 14 and the tubular body 24 of the outer member 13. As shown in FIG. 3, the proximal end 27 of the penetrating tip 14 is provided with a first circular groove 28 which is configured to receive the distal end of the accessing cannula 15 as shown in FIGS. 1 and 3 and a second circular groove 29 which is configured to receive the distal end of tissue cutter 17. The penetrating distal tip 14 may have a variety of tip shapes in addition to the conical shape shown and may have an arcuate RF electrode such as disclosed in U.S. Pat. No. 6,261,241, and co-pending application Ser. No. 09/477,255, filed on Jan. 4, 2000, both assigned to the present assignee. The width and length of the strut 26 preferably is sufficient to provide required support to the distal tip 14. A stiffening rib may be provided to the underside of the strut for structural stiffness. Multiple struts may be used, provided that a large enough opening is available for tissue access to the aperture 16 of the accessing cannula 15.

As best shown in FIGS. 4 and 5, the accessing cannula 15 has a tubular body 30 which defines at least in part the tissue receiving aperture 16. The tubular body 30 has an inner lumen 31 which is configured to slidably receive the tissue cutter 17. The aperture 16 is configured to receive tissue for the specimen of suitable size. The arcuate length of the side edges 32 and 33 forming the aperture 16. The cannula 15 is configured at its proximal end to be operatively connected to a drive unit (not shown) to rotate the tubular body 30 about longitudinal axis 34 to provide a desired orientation to the aperture 16.

The tissue cutter 17, as depicted in FIGS. 6 and 7, is formed of tubular member 35 which has an inner lumen 36 and which has an arcuate wall portion 37 forming side cutting surface 18. The tissue cutting surface 18 may be a sharpened edge of the arcuate wall portion 37 or it may be a blade (not shown) secured to the edge. The cutting surface 18 should be longer than the length of the aperture to ensure complete severance of the tissue specimen from the supporting tissue at the target site upon rotation of the cutting surface 18. The tissue cutter 17 is rotated to effect tissue cutting by cutting surface 18, but the member may also be provided with reciprocating longitudinal movement in addition to the rotational movement thereof to provide a cleaner tissue cut. Both edges of the arcuate wall portion 37 may be sharpened or provided with blades to be cutting surfaces.

Figure 8:
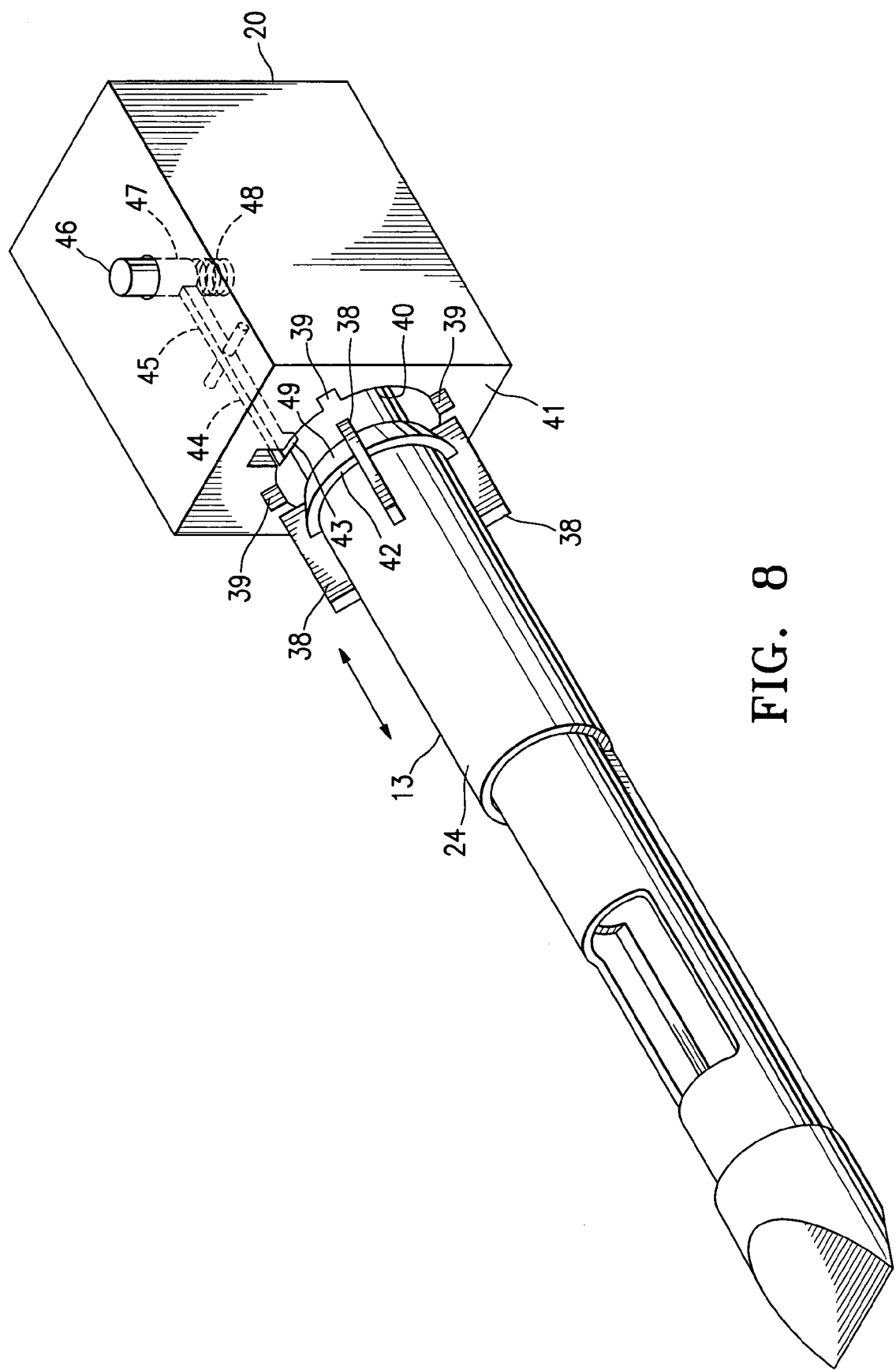
FIG. 8 is a perspective view of the proximal end of the biopsy device illustrating the releasable connection between the proximal end of the probe and the housing.

FIGS. 1 and 8 illustrate the releasable connection between the outer member 13 and the housing 20 to allow for a plurality of discrete orientations of the tissue receiving space of the outer member. As shown, the proximal end of the tubular portion 24 of outer member 13 is provided with a plurality of longitudinally extending upstanding ribs 38 spaced about the periphery of the tubular portion 24. A corresponding number of recessed passageways 39 are disposed about the opening 40 in the distal face 41 of housing 20 designed to receive the ribs 38. Arcuate ridges 42 are provided between the ribs 38 to receive tooth 43 of releasable locking mechanism 44 provided in the interior of housing 20. The mechanism 44 for releasably locking the proximal end of the outer member 13 may take a variety of configurations. The particular mechanism 44 shown in FIG. 8 is preferably manually operated by the fingers of the operating physician. The operator 45 is pivotally connected within the housing 20 at an intermediate location so that downward pressure on button 46 in the top portion of the housing 20 connected to elongated member 47 presses the proximal end of operator 45 raising the distal end and the tooth 43 to release the tooth 43 from the ridge 42 to allow for movement of the proximal end of tubular portion 24 of outer member 13 with respect to the housing 20. The distal end of the mechanism 44 is biased upwardly by spring 48 so that when the proximal end of the outer member 13 is inserted into opening 40 the tooth 43 rides up ramping surface 49 on the proximal end of the ridge 42 and seats and is locked on the front face of ridge 42.

The drive housing 20 and attached probe 11 allows the entire unit to be disposable. The drive units within the housing control the motion of the accessing cannula 15 to orient the aperture 16 and the motion of the cutting member 17 which may be rotation or rotation and longitudinal reciprocation. Other means (not shown) may provide mechanical and electrical power, vacuum, and control to the probe device. Examples of replaceable snap-in type drive units are disclosed in Burbank et al., U.S. patent application Ser. No. 10/179,933, "Apparatus and methods for Accessing a Body Site" hereby incorporated by reference in its entirety. Drive units such as that described in WO 02/069808 (which corresponds to co-pending U.S. application Ser. No. 09/707,022, filed Nov. 6, 2000 and U.S. application Ser. No. 09/864,021, filed May 23, 2001), which are incorporated herein by reference, may be readily modified by those skilled in the art to accommodate the movement of the accessing cannula 15 and the cutting member 17.

FIGS. 9A and 9B, 10A and 10B and 11A and 11B schematically illustrate the operation of the device 11 and the rotation of the probe 12 to discrete orientations. This series of sketches depict the sequencing of taking tissue specimens from below or the bottom side of a target site. In FIG. 9A the aperture 16 is open to the left with the arcuate wall portion 40 in a non cutting position. A vacuum is applied to the inner lumen 31 of the tissue cutter 17 and tissue 50 (shown in phantom) from the target site is pulled into the interior of the accessing cannula 15 through the aperture 16. In FIG. 9B the arcuate portion 37 of tissue cutter 17 is rotated to sever the aspirated tissue 50 from the supporting tissue at the target site with the cutting surface 18. The vacuum within the inner lumen 31 of the tissue cutter 17 pulls the tissue specimen through the inner lumen and into the collection station 21 shown in FIG. 1. The accessing cannula 15 is then rotated so that the aperture 16 is facing upwardly as shown in FIG. 10A and as shown in FIG. 10B the procedure for cutting the tissue specimen is repeated. In FIGS. 11A and 11B the aperture 16 is open to the right and the procedure is again repeated for additional specimens. Other intermediate positions for the aperture 16 are possible. When the target site is accessed from the upper portion thereof, the probe device 11 is released from the housing 20 and then is inverted or turned through 180° so that the strut 26 is on top as shown in FIGS. 12A and 12B with the aperture 16 open downwardly. The housing 20, not shown in these drawings, may remain in the same orientation. The same motion for the accessing cannula 15 as described above may be used to obtain a similar series of tissue specimens from the top of the target site. If the target site is large enough, the probe may pass through the site and accessing may occur from within the interior of the target site in the same or similar manner as that discussed above for accessing the tissue from the top or bottom of the tissue site.

Figure 13:
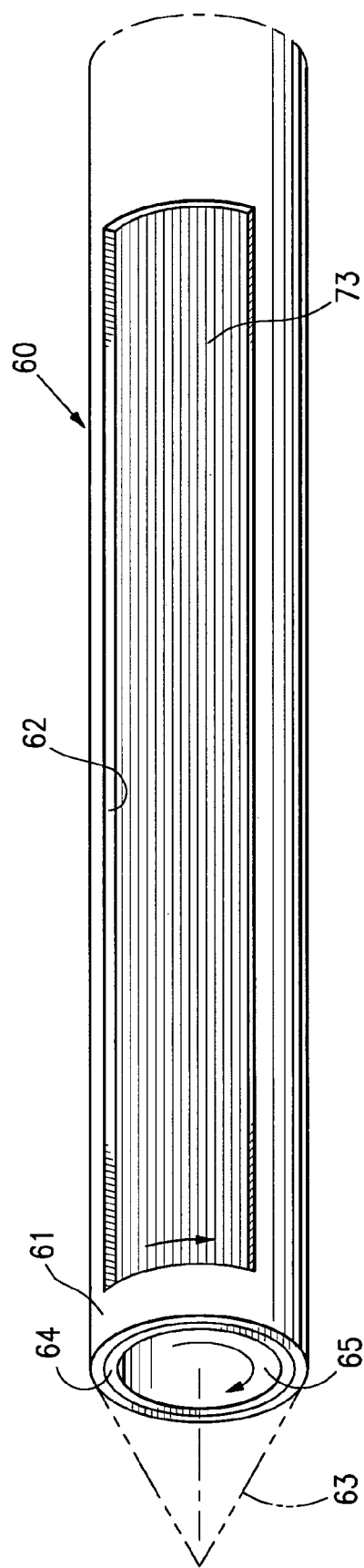
FIG. 13 is a perspective view of the distal portion of an alternative design for the probe embodying features of the invention in a closed condition.
Figure 14:
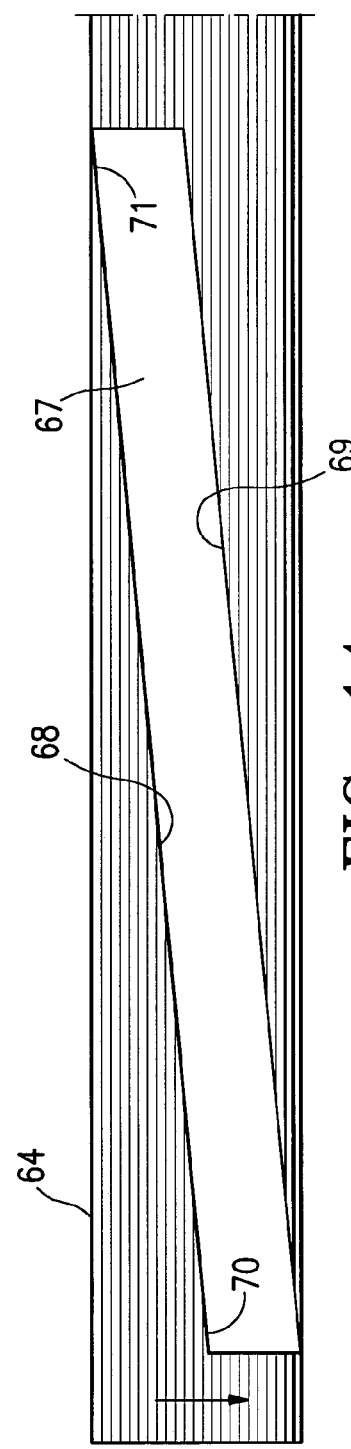
FIG. 14 is a top plan view of the tissue cutter of the probe shown in FIG. 13.
Figure 15:
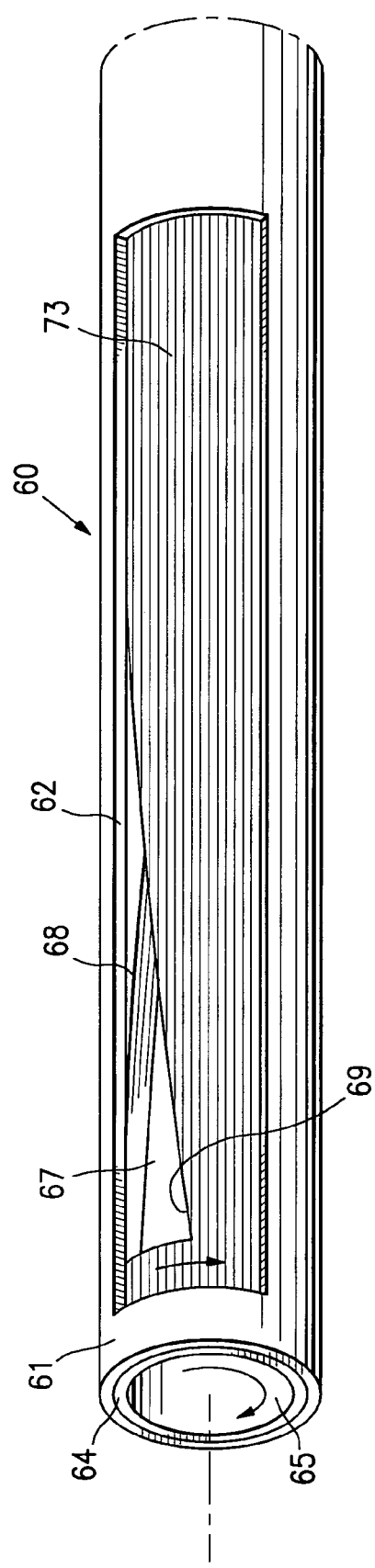
FIG. 15 is a perspective view of the probe shown in FIG. 13 partially open.
Figure 16:
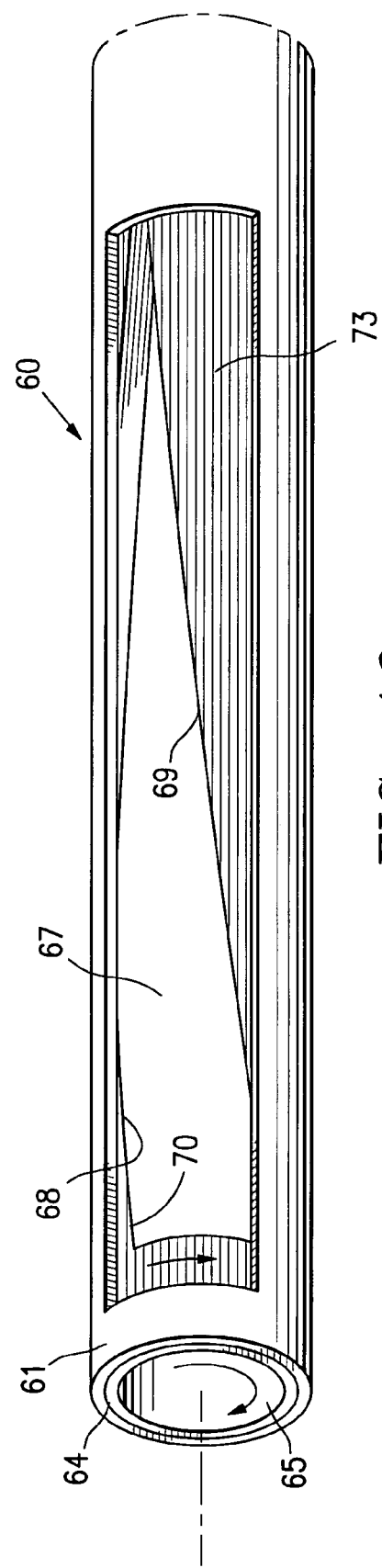
FIG. 16 is a perspective view of the probe shown in FIG. 13 with the leading distal cutting edge depicted.

FIGS. 13–18 illustrate a probe 60 for a biopsy device embodying features of the invention. In probe 60 the outer member or cannula 61 has a tissue receiving aperture 62 for receiving tissue from the target site. The outer member 61 has a sharp distal tip 63 shown in phantom which is configured to easily penetrate through tissue to the target site. Tissue cutter 64 is rotatably disposed within outer member 61 and has a proximal end (not shown) operatively connected to one or more drive units within housing (not shown) for imparting cutting motion thereto such as previously described herein. The inner lumen 65 of tissue cutter 64 is configured for fluid communication with a vacuum source (not shown) to urge a tissue specimen through the inner lumen 65. The tissue cutter 64 has an aperture 67 as shown in FIG. 14 defined in part by cutting edge 68 and non-cutting edge 69. The cutting surface is longitudinally oriented at an angle with respect to the longitudinal axis of the tissue cutter 64. The cutting surface or edge 68 has a distal leading cutting edge portion 70 and a proximal trailing cutting edge portion 71. This tissue cutter structure provides better application of vacuum to tissue at the target site and as a result provides better control of the tissue cutting. The cutting action is shown in the sequence shown in FIGS. 13 and 15–18. In FIG. 13, the aperture 62 of the outer member 61 is closed by the arcuate wall portion 73 of tissue cutter 64. The non-cutting edge 69 of tissue cutter 64 first appears at the distal end of aperture 67 as shown in FIG. 15. Application of vacuum begins to pull tissue from the target site into the interior of the tissue cutter at the distal location. As the tissue cutter 64 rotates (as shown in FIGS. 16–18) the non-cutting edge 69 first appears to allow tissue to be pulled into the inner lumen 65 of the tissue cutter and the cutting edge 68 of the tissue cutter follows, cutting off tissue pulled into the interior of the cutter from the supporting tissue at the target site starting from the leading cutting edge portion 70 to the trailing proximal cutting edge portion 71 along the length of the aperture 67.

Figure 19:
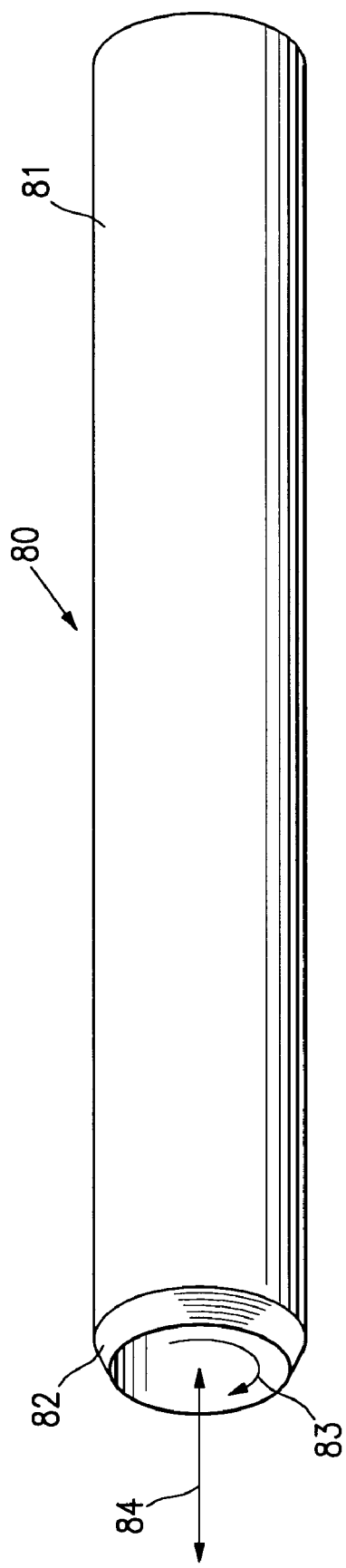
FIG. 19 is a perspective view of the distal portion of an alternative tissue cutting cannula suitable for use in the biopsy device shown in FIG. 1.

FIG. 19 illustrates an alternative cutting member 80 which is formed of tubular member 81 and which has a sharpened distal end 82. The cutting member 80 may be advanced distally to sever tissue which has been pulled into the accessing cannula 15 through the aperture 16. The cutting member 80 may also be rotated continuously in one direction or be provided with reciprocating rotary motion in addition to the longitudinal motion to facilitate tissue cutting as shown by the arrows 83 and 84.

The elongated shaft or probe of the biopsy device has a length of about 3 to about 15 cm, preferably, about 5 to about 13 cm, and more specifically, about 8 to about 9 cm for breast biopsy use. To assist in properly locating the probe of the device during advancement thereof into a patient's body, (as described below), the distal extremity of the various members may be provided with markers at desirable locations that provide enhanced visualization by eye, by ultrasound, by X-ray, or other imaging or visualization means. An echogenic polymer coating that increases contrast resolution in ultrasound imaging devices (such as ECHOCOAT™ by STS Biopolymers, of Henrietta, N.Y.) is suitable for ultrasonic visualization. Radiopaque markers may be made with, for example, stainless steel, platinum, gold, iridium, tantalum, tungsten, silver, rhodium, nickel, bismuth, other radiopaque metals, alloys and oxides of these metals. In addition, the surfaces of the device in contact with tissue or other components of the device may be provided with a suitable lubricious coating such as a hydrophilic material or a fluoropolymer.

The outer member or cannula, the accessing cannula and the tissue cutter are preferably formed of stainless steel. However, other high strength materials such as MP35N, other cobalt-chromium alloys, NiTi alloys, ceramics, glasses, and high strength polymeric materials or combinations thereof may be suitable.

A patient's skin usually must be breached in order to gain access to a body site where a tissue specimen is to be obtained. A scalpel or other surgical instrument may be used to make an initial incision in the skin. After the specimens have been taken, the biopsy device may be removed from the patient. The entire device may be removed; however, in preferred embodiments, the outer member may remain within a patient's body to aid, for example, in the acquisition of further tissue specimens and in the placement of markers at the site from which a tissue sample was taken. In addition, it will be readily appreciated that other types of instruments may be inserted into the tissue site through the fixed outer cannula or accessing cannula in addition to or in place of the instruments described above.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention to be defined by the scope of the appended claims as broadly as the prior art will permit.

Terms such a "element", "member", "device", "sections", "portion", "section", "steps" and words of similar import when used herein shall not be construed as invoking the provisions of 35 U.S.C. §112(6) unless the following claims expressly use the terms "means" or "step" followed by a particular function without specific structure or action. All patents and patent applications referred to above are hereby incorporated by reference in their entirety. Accordingly, it is not intended that the invention be limited, except as by the appended claims.

What is claimed is:

1. An tissue biopsy device for accessing and collecting a tissue specimen from a target site within a patient, comprising:
   a. a housing having at least one drive unit;
   b. an elongated probe member which has a longitudinal axis, which has a proximal end configured to be releasably secured to the drive housing in a plurality of discrete orientations about the longitudinal axis prior to insertion into the patient's body, which has an inner lumen extending therein, which has a tissue penetrating distal tip and which has an open section proximal to the tissue penetrating distal tip configured to receive tissue from the target site; and
   c. an elongated tissue cutter which is slidably disposed within the elongated probe member, which has a tissue cutting surface, which defines at least in part an inner lumen extending therein for receiving a tissue specimen, which is operably connected to at least one drive unit to move the tissue cutter to cut a tissue specimen from tissue extending into the open tissue receiving section of the elongated member; and
   d. a rotatable tissue accessing cannula which is slidably disposed concentrically about the tissue cutter, has a proximal end, has a distal end seated against a proximal surface of the tissue penetrating distal tip, has an inner lumen extending therein, has a tissue receiving side port spaced proximal to the distal end thereof in fluid communication with the inner lumen and disposed in the open section of the outer cannula and is operably secured to a drive unit in the housing to rotate the tissue accessing cannula to adjust the operating location of the tissue receiving side port.

2. The biopsy device of claim 1, wherein the cutting surface of the tissue cutter is longitudinally oriented.

3. The biopsy device of claim 1, wherein the cutting surface of the tissue cutter is defined at feast in part by an arcuate wall section of the tissue cutter.

4. The biopsy device of claim 2 wherein the arcuate wall section of the tissue cutter has a longer arc length than the arc length of the aperture.

5. The biopsy device of claim 1, wherein the cutting surface of the tissue cutter is longer than the aperture of the tissue accessing cannula.

6. The biopsy device of claim 1 wherein the inner lumen defined at least in part by the tissue cutter is configured to access a vacuum source to transport a tissue specimen through the inner lumen thereof to a tissue collector in fluid communication with the inner lumen.

7. The biopsy device of claim 1, wherein the tissue cutter is configured for rotational movement about a longitudinal axis.

8. The biopsy device of claim 7, wherein the tissue cutting member is also configured for reciprocating longitudinal movement.

9. The biopsy device of claim 8, wherein the tissue cutter is configured for recipmcating longitudinal movement of between about 0.01 inch and about 0.1 inch.

10. The biopsy device of claim 2, wherein the arcuate wall section of the tissue cutter has longitudinally oriented cutting surfaces along both edges.

11. The biopsy device of claim 1 wherein the cutting surface of the tissue cutter is longitudinally oriented at an angle with respect to the longitudinal axis of the tissue cutter.

12. The biopsy device of claim 11 wherein the cutting surface of the tissue cutter has a leading distal cutting edge portion and a trailing proximal cutting edge portion.

13. The biopsy device of claim 11 wherein the tissue cutter has a non-cutting surface which extends parallel with the cutting surface.

14. The biopsy device of claim 13 wherein the cutting and non-cutting surfaces of the tissue cutter define in part a tissue receiving aperture.

15. The biopsy device of claim 1, wherein the tissue cutter is configured for longitudinal movement along a longitudinal axis.

16. The biopsy device of claim 15, wherein the tissue cutting member is also configured for recipmcating rotational movement.

17. A tissue biopsy device for accessing and collecting a tissue specimen from a target site within a patient, comprising:
 a. a drive housing which has a plurality of drive units;
 b. an outer member which is releasably secured to the drive housing, which has a proximal tubular portion, which has an inner lumen extending within the proximal tubular portion, which has a tissue penetrating distal tip, which has an open section proximal to the tissue penetrating distal tip and which has a supporting strut extending from the penetrating distal tip to the proximal tubular portion;
 c. a tissue accessing cannula which is slidably disposed at least in part within the inner lumen of the proximal tubular portion of the outer member, which has an inner lumen extending therein, and which has a tissue receiving aperture spaced proximal to the distal end thereof in fluid communication with the inner lumen of the accessing cannula and which is operably secured to a drive unit in the drive housing to rotate the tissue receiving cannula to adjust the orientation of the tissue receiving aperture; and
 d. an elongated tissue cutter which is formed at least in part of a tubular member, which is slidably disposed within the inner lumen of the tissue accessing cannula, which has a tissue cutting surface, which has an inner lumen extending therein configured to receive a tissue specimen cut by the tissue cutter, and which is connected to a drive unit to move the tissue cutter within the inner lumen of the tissue accessing cannula.

18. The biopsy device of claim 17, wherein the cutting surface is parallel to a longitudinal axis of the tissue cutter.

19. The biopsy device of claim 17, wherein the cutting surface of the tissue cutter is defined at least in part by a arcuate wall section thereof.

20. The biopsy device of claim 17 wherein the arcuate wall section of the tissue cutter has a longer arc length than the arc length of the tissue receiving aperture of the tissue accessing cannula.

21. The biopsy device of claim 17, wherein the cutting surface of the tissue cutter is longer than the aperture of the tissue accessing cannula.

22. The biopsy device of claim 17 wherein the tissue accessing cannula has a distal end seated against a proximal surface of the tissue penetrating distal tip of the outer member.

23. The biopsy device of claim 17 wherein the tissue accessing cannula has a distal end seated in a circular groove in a proximal surface of the tissue penetrating distal tip of the outer member.

24. The biopsy device of claim 17 wherein the inner lumen of the tissue cutter is configured to access a vacuum source to transport a cut tissue specimen through the inner lumen thereof to a tissue collector in fluid communication with the inner lumen of the tissue cutter.

25. The biopsy device of claim 17 wherein the arcuate wall section of the tissue cutter has an arc length greater than a width of the aperture in the outer member.

26. The biopsy device of claim 17, wherein the tissue cutter is configured for longitudingal movement along a longitudinal axis.

27. The biopsy device of claim 17, wherein the tissue cutter is configured for reciprocal longitudinal movement.

28. The biopsy device of claim 17, wherein the tissue cutter is configured for reciprocal longitudinal movement of between about 0.01 inch and about 0.1 inch.

29. The biopsy device of claim 17, wherein the arcuate wall section of the tissue cutter has longitudinal oriented cutting surface along both edges.

30. A probe for a tissue biopsy device for accessing and collecting a tissue specimen from a target site within a patient, comprising:
 a. an outer member which has a proximal tubular portion configured to be releasably secured to a drive housing, which has an inner lumen extending therein, which has a tissue penetrating distal tip, which has an open section proximal to the penetrating distal tip and a supporting strut extending from the penetrating distal tip to the proximal tubular portion;
 b. a tissue accessing cannula which is slidably disposed at least in part within the inner lumen of the tubular portion of the outer member, which has an inner lumen extending therein, and which has a tissue receiving aperture spaced proximal to the distal end thereof in fluid communication with the inner lumen of the accessing cannula and which is configured to be operably secured to a drive unit in a drive housing to rotate the tissue receiving cannula to adjust the orientation of the tissue receiving aperture; and
 c. an elongated tissue cutting member which is slidably disposed within the inner lumen of the tissue accessing cannula, which has at least one longitudinal tissue cutting surface, which defines at least in part an inner lumen for receiving tissue cut by the tissue cutting surface, and which is connected to a drive unit to move the tissue cutter within the inner lumen of the tissue accessing cannula.

31. The probe of claim 30 wherein the tissue cutting member is formed at least in part of a tubular member.

32. The probe of claim 31 wherein the tissue cutter is rotatably disposed within the inner lumen of the outer member, has a longitudinal axis, has a longitudinal tissue cuffing surface oriented at an angle with respect to the longitudinal axis, has an inner lumen extending therein for receiving tissue cut by the tissue cutting surface and is configured for rotation within the inner lumen of the outer member to cut tissue pulled into the inner lumen of the tissue cutter.

33. The biopsy device of claim 32 wherein the tissue cutter has a non-cutting surface which defines a tissue receiving aperture along with the tissue cutting surface.

34. The biopsy device of claim 33 wherein the non-cutting surface of the tissue cutter is parallel with the cutting surface thereof.

35. The biopsy device of claim 30 wherein the cutting surface of the tissue cutter has a leading distal cutting edge portion and a trailing proximal cutting edge portion.

36. A method of separating a biopsy tissue specimen from supporting tissue at a target site within a patient's body, comprising:
   a. providing a biopsy device having a biopsy probe comprising:
      i. an outer member which is releasably secured to a drive housing, which has an inner lumen extending therein, which has a tissue penetrating distal tip secured thereto, which has an open section proximal to the penetrating distal tip and a supporting strut extending from the penetrating distal tip;
      ii. a tissue accessing cannula which is slidably disposed at least in part within the inner lumen of the outer member, which has an inner lumen extending therein, and which has a tissue receiving aperture spaced proximal to the distal end thereof in fluid communication with the inner lumen of the accessing cannula and which is operably secured to a drive unit in the drive housing to rotate the tissue receiving cannula to adjust the orientation of the tissue receiving aperture, and
      iii. an elongated tissue cutting member which is formed at least in part of a tubular member, which is slidably disposed within the inner lumen of the tissue accessing cannula, which has at least one tissue cutting surface, which has an inner lumen extending therein for receiving a tissue specimen cut by the tissue cutting surface, and which is connected to a drive unit to move the tissue cutter within the inner lumen of the tissue accessing cannula;
   b. advancing the probe at least partially into or adjacent to tissue at the target site;
   c. exposing the aperture of the accessing cannula to tissue at the tissue site;
   d. applying a vacuum to the inner lumen of the tissue accessing cannula or the tissue cutter to draw tissue from the tissue site into the inner lumen of the accessing cannula;
   e. rotating the tissue cutter to cut tissue drawn into the inner lumen from supporting tissue at the tissue site; and
   f. transporting a tissue specimen through the inner lumen of the tissue cutter.

37. The method of claim 36, wherein the tissue cutter is moved longitudinally in addition to rotating to cut tissue.

38. The method of claim 36, wherein the longitudinal movement of the tissue cutter is reciprocating movement.

39. The method of claim 36, wherein pressurized fluid is provided within the inner lumen of the tissue cutter distal to a tissue specimen therein to transport the tissue specimen proximally within the inner lumen of the tissue cutter.

* * * * *